(12) United States Patent
Wilson

(10) Patent No.: US 7,685,011 B2
(45) Date of Patent: Mar. 23, 2010

(54) METHOD AND SYSTEM FOR OPTIMIZING RESOURCE ALLOCATION BASED ON COHORT TIMES

(76) Inventor: Thomas W. Wilson, 809 Almahurst La., Loveland, OH (US) 45140

( * ) Notice: Subject to any disclaimer, the term of this patent is extended or adjusted under 35 U.S.C. 154(b) by 1645 days.

(21) Appl. No.: 10/693,790

(22) Filed: Oct. 25, 2003

(65) Prior Publication Data
US 2005/0091094 A1 Apr. 28, 2005

(51) Int. Cl.
*G06F 17/50* (2006.01)
(52) U.S. Cl. ............... 705/7; 705/8; 705/2; 705/500
(58) Field of Classification Search ............ 705/7
See application file for complete search history.

(56) References Cited

U.S. PATENT DOCUMENTS

| 5,692,125 | A | * | 11/1997 | Schloss et al. | 705/9 |
| 5,778,345 | A | * | 7/1998 | McCartney | 705/2 |
| 5,976,082 | A | * | 11/1999 | Wong et al. | 600/300 |
| 6,223,164 | B1 | * | 4/2001 | Seare et al. | 705/2 |
| 2003/0065534 | A1 | * | 4/2003 | McCartney | 705/2 |

OTHER PUBLICATIONS

Rohrer, J.E. "Duration of heart disease visits by elderly patients: productivity versus quality" Health Services Management Research, Aug. 2002, p. 141-146.*
http://www.phiinstitute.org/evaluation.html (4 of 4)Jan. 4, 2008 3:40:51 PM.*
Lynch, John W. et al. "Childhood and adult socioeconomic status as predictors of mortality in Finland", The Lancet, Feb. 26, 1994, p. 524.*
Wilson, Thomas; "Evaluating ROI in State Disease Management Programs" State Coverage Initiatives, vol. IV, No. 5, Nov. 2003.*
Geskus, R. "Methods for estimating the AIDS incubation time distribution when date of seroconversion is censored" (2001), Statistics in Medicine, Statist. Med. 2001; 20:795-812.*

(Continued)

*Primary Examiner*—Bradley B Bayat
*Assistant Examiner*—Mark A Fleischer
(74) *Attorney, Agent, or Firm*—Mark F. Smith; Smith Brandenburg Ltd

(57) ABSTRACT

The present invention is a method for improving resource allocation comprising the steps of identifying at least one criteria; Identifying sets of information wherein each set of information includes a unique unit of analysis (UOA-ID), a calendar/clock time (CCT), a CATVAR and a VAR Value; grouping each UOA-ID into an appropriate specific population (Type); identifying a Start Time wherein each UOA-ID has met said at least one criteria; forming at least one prospective or retrospective Cohort time segment for each UOA-ID based on their Start Time; placing the UOA-ID into the appropriate time segment; calculating an eligibility score for each UOA-ID for each time segment; calculating an Eligible Adjusted Variable Value; and generating at least one Output Expression that can be subdivided by each CATVA.

19 Claims, 8 Drawing Sheets

OTHER PUBLICATIONS

Gordin, Fred, et al. "Early Manifestations of Disseminated Mycobacterium avium Complex Disease: A Prospective Evaluation", The Journal of Infectious Diseases 1997;176:126-32 by the University of Chicago.*

Goggins, William, et al. "Applying The Cox Proportional Hazards Model for Analysis of Latency Data With Interval Censoring", Statistics in Medicine Statist. Med. 18, 2737-2747 (1999).*

Kim, S. et al. "Strategies for Cohort Sampling Under the Cox Proportional Hazards Model, Application to an AIDS Clinical Trial", Lifetime Data Analysis, 5, 149-172 (1999) Kluwer Academic Publishers, Boston. Manufactured in The Netherlands.*

Gordin, Fred, et al. "Early Manifestations of Disseminated Mycobacterium avium Complex Disease: A Prospective Evaluation", The Journal of Infectious Diseases 1997;176:126-32 by The University of Chicago.*

\* cited by examiner

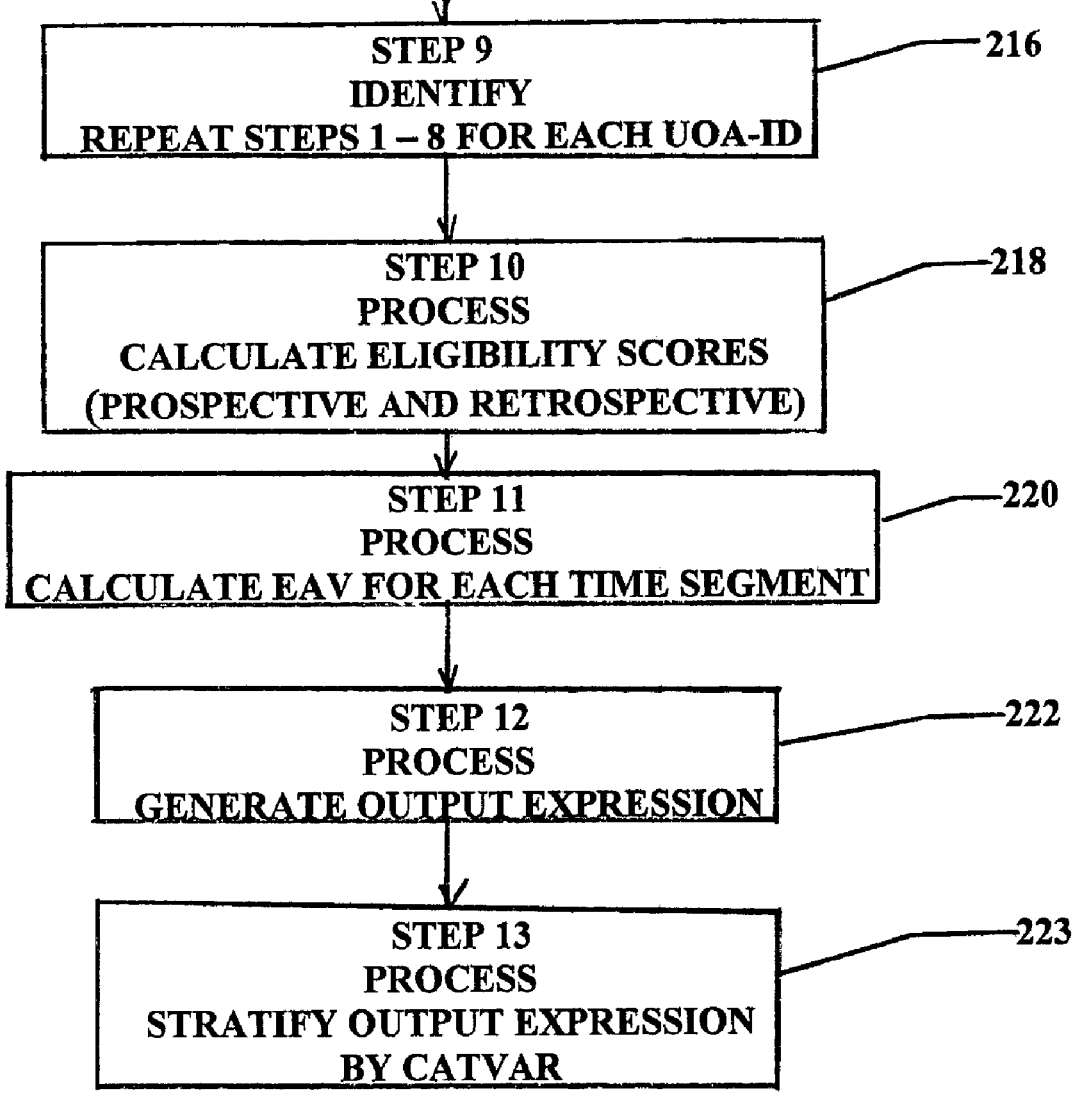

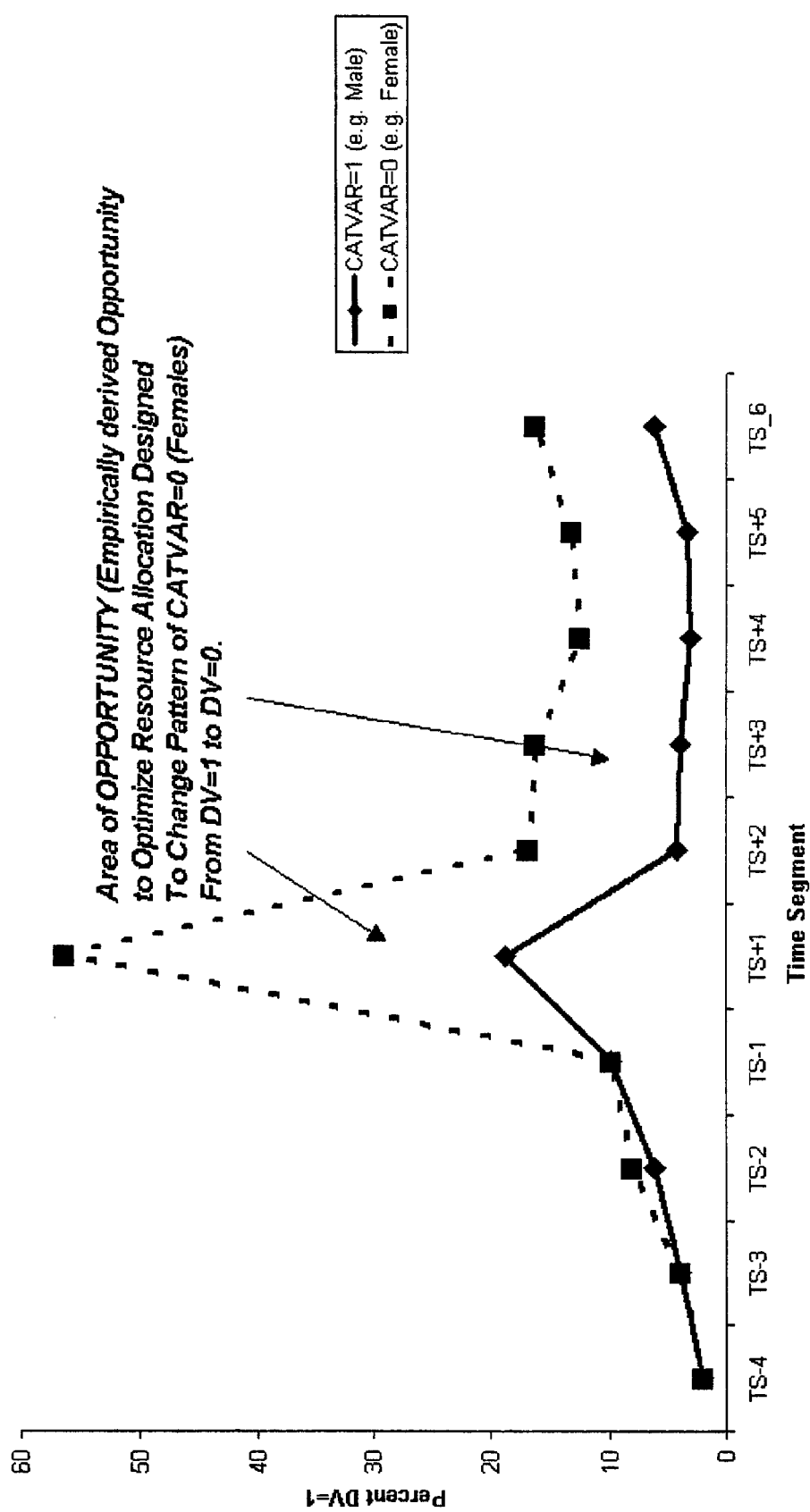

METHOD AND SYSTEM FOR OPTIMIZING RESOURCE ALLOCATION BASED ON COHORT TIMES

RELATED PATENT APPLICATIONS

The present application deals with related subject matter in co-pending patent application filed under the PCT application no. PCT/US02/21225 entitled Method and System for Analyzing Resource Allocation and U.S. provisional patent application Ser. No. 60/420,878 filed Oct. 24, 2002, entitled Strategies for Assessing Causality in Disease Management Programs.

BACKGROUND OF THE INVENTION

The present invention related to a method and system for allocating resources to achieve specified outcomes and, more particularly, to a method and system for analyzing data for allocating resources over time for defined populations to achieve specified outcomes to best serve a business' goals.

Managing a business or an organization in a manner that creates long term value is a complex activity. Further, every business or organization has limited resources and the need for business to accurately monitor their costs and justify resource allocation to achieve specified outcomes in a further calendar time period (e.g. financial quarters) is becoming increasingly important. Unfortunately, the task or organization business information to determine proper resource allocation is often extensive and troublesome to organize and it is often difficult or impossible for business managers to use this information to make proper decisions. Accordingly, businesses and other organizations typically either overspend their resources or do not avail themselves for statistical data and analysis that can be used to optimize their resource expenditures. For example, business establishments that serve a large number of customers generally have a problem analyzing their transactional information to develop trends in defined population overtime. Such trends are desirable to effectively target and determine the effectiveness of various programs for the purposes of optimizing resource allocation to achieve specified outcomes over designed time periods. Further, while it may be known that certain cost reduction programs are hypothesized to be effective to reduce future costs, a need exists for an effective and scientific method and system for optimizing resource allocation that can be shown to likely achieve specified outcomes over time to maximize a business's investment.

Until now, most economic business models have relied on "calendar time" in determining resource allocation rather than using "experience time" where time is based on the start of an event and its duration (such as the day one purchased a car or the date/time an individual was bitten by a malarial infected mosquito, starting the individual on a "natural" course of fluctuating fevers). Thus, the experience of a population in any calendar time period will vary depending on when each individual "started" in this population. Accordingly, a business organization will be better able to analyze and evaluate the resources that will be necessary to achieve a specific outcome by first understanding this "Cohort Time" heterogeneity of any population during any calendar (or clock) time period and then subdividing the populations into subgroups, or strata, to determine which subgroup, if any, offers the optimal opportunity for resource expenditure.

By way of illustration, manufactures, such as automobile manufactures, are actively searching for ways to reduce the probability of realizing extensive repair costs under warranty. Despite dramatic improvement in new-vehicle quality at most major automobile manufacturers over the past decade, the reduction of warranty cost is a large area for potential cost reductions. While manufactures have developed sophisticated statistical tracking systems, until now there was no adequate method or system to assess available resources today to reduce specified outcomes (i.e., warranty costs) in the future and to target subgroups within the car buying public that offer an optimal resource allocation opportunity.

Recently, the optimization of resource allocation has been particularly important for businesses engaged in the healthcare industry. Due to significant increases in health care costs, health care providers and service management organizations have become under increased pressure by customers to find ways of lowering, or at least slowing, the rate of growth of health care costs. As a result of such pressure, health care providers have implemented numerous population-based programs, such as wellness programs, disease management programs, and other health-inducing and cost-reduction programs, designed to improve the overall health of the population thereby reducing, at least theoretically, overall health care costs. Such health care organizations, however, are in need of a system that can qualitatively better understand the performance of programs and also analyze program performance in order to optimize allocation of health care services and expenditures over time to achieve specified outcomes.

Currently, such as in health care an "individual unit" with a certain characteristic that makes it eligible for inclusion in a defined population, is entered into the population at a certain "start time" (clock or calendar time) and remains "eligible" for this population during a known and quantifiable duration of time. Furthermore, this population has a greater than zero probability of experiencing some event at a future time period, an event with some economic value attached to it. This event, the "individual unit," the date of the event, and the "cash value" of such event is captured by a transaction system. In addition, categorical or stratifying variables are also captured by this transactional system or can be inputted from other systems (e.g. health risk assessments, or electronic medical records) and the entire defined population can be subdivided to learn where the optimal opportunity lies. For example, look at the cohort time trends of a defined population with congestive heart failure when subdivided by a fixed categorical variable: Gender. We may find that all other things being equivalent (e.g. age, # of comorbidities, etc.) females have higher resource expenditure than males and the expected absolute percent change following an intervention would be higher in females than in males. Thus, the female category would be considered a higher opportunity to target, thus, the invention could allocate resource where they would do the most good.

The same concept can be seen with a categorical variable that is dynamic (CATVAR-dynamic) like the date that a 30 day prescription is filled. Say, we have 6 time segments of 30 days each. There are three general possibilities over these 6 times segments made of "0s" for Not filled and "1s" for filled for six different time segments each represented by an integer place holder (this assumes no missing information, that is also a possibility that this invention can accommodate). The Rx is filled for all six time segments (111111), the Rx is filled for no time segments (000000), the Rx is filled for some time segments and not for others (e.g. 010101 or 101010 or 000001 or 100000 etc). The final stratification could be three fold, for example: those who were compliant for all six times segments, vs. those where were partially compliant vs. those what were not compliant at all (there are numerous other possibilities). If the output revealed a similar outcome from the fully compliant to the partially compliant but a worse outcome for the non-compliant this would provide empirical support for an initiative to take medication vs. intervention to get the partially compliant fully compliant.

The method and apparatus transforms this information into usable estimates for of resource allocation needed to achieve specified outcomes. Accordingly, a need exists for an improved method and system to qualitatively analyze cost reduction programs and for analyzing information for allocating resources to best serve a business' goals and then optimize such resource allocation.

SUMMARY OF THE INVENTION

The present invention provides a method for optimizing resource allocation. In a preferred embodiment of the invention the method uses a set of information, and comprises analyzing resource allocation by the steps of identifying an Unit of Analysis Identifier, a Type, a clock or calendar time, a categorical variable(s) to enable stratification, and a Variable Value for each set of information; grouping and organizing each Unit of Analysis Identifier into an appropriate Type; identifying a Start Time; identifying a time segment period; forming time segments based on the Start Time; adjusting (e.g. for economic inflation) and standardizing (e.g. for actual eligibility) each Variable Value to create Adjusted Variable Values; placing each Adjusted Variable Value into the appropriate time segment; calculate an eligibility-adjusted score for each Unit of Analysis Identifier for each time segment; and generating an Output Expression; then stratifying the output expressions to ensure the discovery of the optimal high opportunity subpopulation for the optimization of resources.

In another preferred embodiment of the invention the method of analyzing resource allocation further includes the step of transforming the Output Expression from being expressed in Cohort time segments to being expressed in COT segments.

In another embodiment of the invention the method for optimizing resource allocation is performed using a system comprising a central processing unit for implementing system software effective for performing the method.

Another preferred embodiment of the invention, a system for optimizing resource allocation comprises a central processing unit for operating software effective for performing the method of grouping data identified by the user into appropriate Groupers (Grouper can be equivalent to type, in that case it is a many-to-few algorithm); identifying a Start Time; forming at least one Cohort time segment based on the Start Time; adjusting and standardizing the information and placing the information into the appropriate time segment; calculating an eligibility score for the information for each time segment; generating at least one Output Expression and stratifying the output expression based upon a Categorical variable into two or more mutually exclusive groupings.

Another preferred embodiment of the invention is an Output Expression for use in optimizing resource allocation comprising a representation showing trends of a particular Population, said trends are expressed in Cohort time segments, and these trends are compared between different levels of the categorical variable.

In another preferred embodiment of the invention, an Output Expression is generated by the method comprising the step of calculating an Eligible Adjusted Variable Value ("EAV") based on a summary metric for each Individual Unit of Analysis ("UOA-ID") per Type and these trends are compared between different levels of the categorical variable.

In another preferred embodiment of the invention, an Output Expression is generated by the method comprising the steps of determining a dichotomous variable ("DV") per Type per time segment; calculating a EAV summary metric for all UOA-IDs per Type per time segment; and calculating an EAV Net Value per Type per time segment and these findings are compared between different levels of the categorical variable.

In another preferred embodiment of the invention the Output Expression is generated by the method comprising the steps of determining a return on resource allocation ("RORA"); determining an Outcome; calculating a number needed to target ("NNT"); calculating an EAV Net Value per Type per time segment; and calculating the maximum available resource allocation ("RA") per UOA-ID per time segment and these findings are compared between different levels of the categorical variable.

In another preferred embodiment of the invention the Output Expression is generated by the method comprising the steps of determining a RA and an Outcome, calculating a NNT, calculating an EAV Net value per Type per time segment and calculating the RORA and these trends are compared between different levels of the categorical variable.

In another preferred embodiment of the invention the Output Expression is generated by the method comprising the steps of determining a RA and a RORA, calculating a NNT, calculating an EAV Net value per Type per time segment and calculating the Outcome and these trends are compared between different levels of the categorical variable.

Other advantages of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIGS. 3a and 3b is a flow diagram illustrating the general functional steps of the system of FIG. 1;

FIG. 7 is an example Output Expression stratified by CATVAR.

DETAILED DESCRIPTION OF THE PREFERRED EMBODIMENTS

Figure 1:
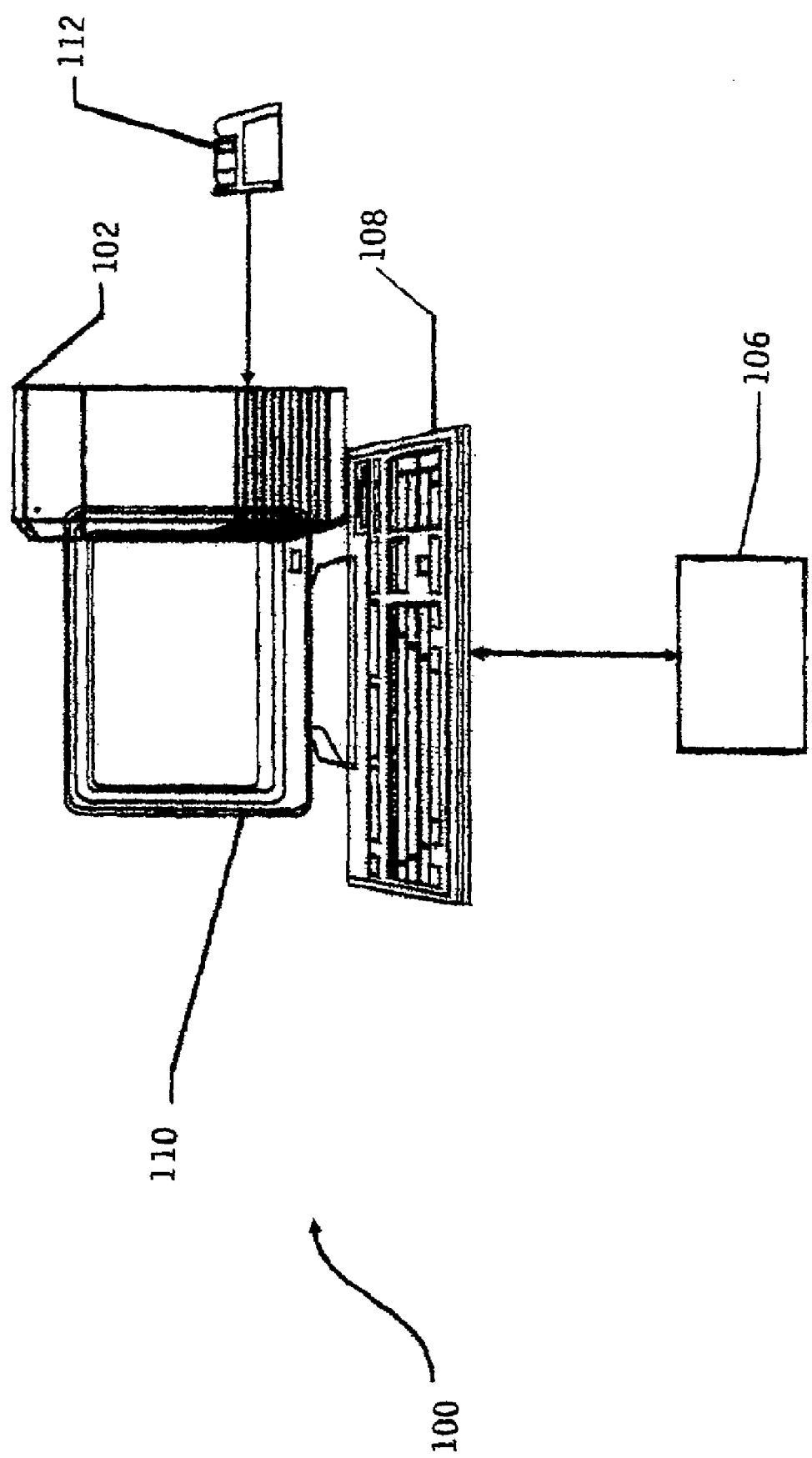
FIG. 1 is a diagrammatic representation of a system for providing a method of optimizing resource allocation in accordance with the present invention.

The present invention relates to a method and system for optimizing resource allocation. In describing the preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose.

Referring to FIG. 1, a preferred embodiment of the system 100 for providing a method of optimizing resource allocation the present invention is shown comprising a central processing unit 102 used to implement the system software 104 (FIG. 2) of the system 100. The central processing unit 102 includes a memory 106 and may be coupled to other devices, such as a suitable input device 108, like a keypad, touch screen, or any other suitable input device that can accept information, and one or more suitable output devices 110, such as a computer or electronic display device, printer, projection device, and the like. It should be understood that the system 100 could include any combination of the above components, or any number of different components, peripherals, and other devices. Preferably, the central processing unit 102 operates under the control of an operating system, such as the WINDOWS™ operating system developed by Microsoft Corporation or the Macintosh™ operating system developed by Apple Computer Corporation or other "mainframe" operating system. It should be understood, however, that other operating systems could be utilized to implement the system software 102 (FIG. 2) of the system 100 of the present invention.

The system software 104 is a computer-readable medium having computer-readable instructions for performing the method of optimizing resource allocation. Preferably, the system software 104 is an interactive, menu and event driven system that uses prompt, dialog, and entry windows to guide a user to enter information. As used herein, the term "software" refers to any form of programmed machine-readable language or instructions (e.g., object code) that, when loaded or otherwise installed, provides operating instructions to a machine capable of reading those instructions, such as a computer. The system software 104 of the present invention can be stored or reside on, as well as be loaded or installed from, various software input devices 112 such as one or more floppy disks, CD ROMS disks, hard disks or any other form of suitable non-volatile electronic storage media. The system software 104 can also be installed by downloading or other form of remote transmission, such as by using Local or Wide Area Network (LAN or WAN)-based, Internet-based, web-based or other remote downloading or transmission methods. Upon a user's entry of appropriate initialization commands entered via the input device 108, the system software 104 is read by the central processing unit 102 and the method of the present invention for optimizing resource allocation is implemented.

Figure 2:
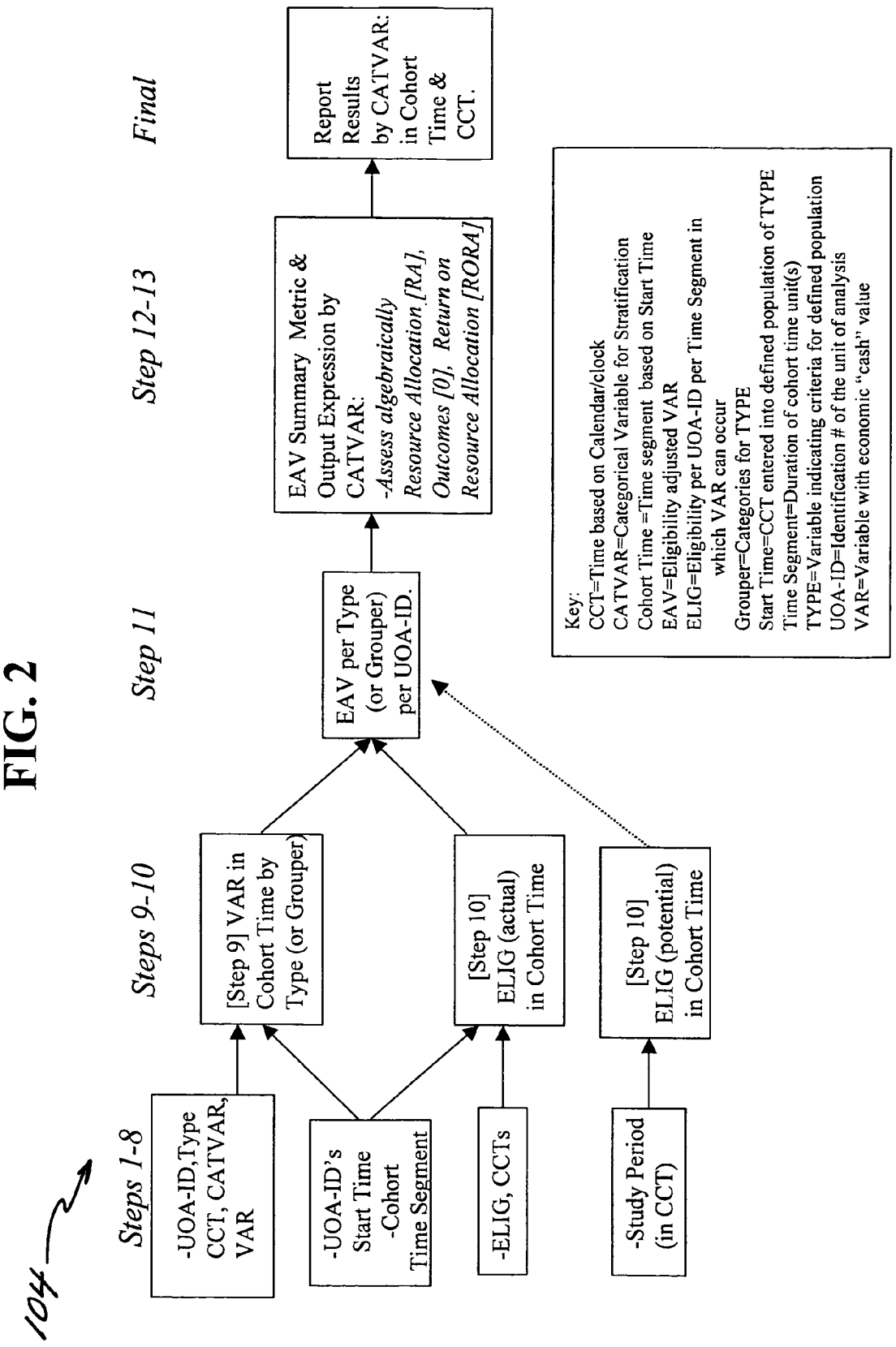
FIG. 2 is a diagrammatic representation showing the general methodology of the present invention.
Figure 3A:
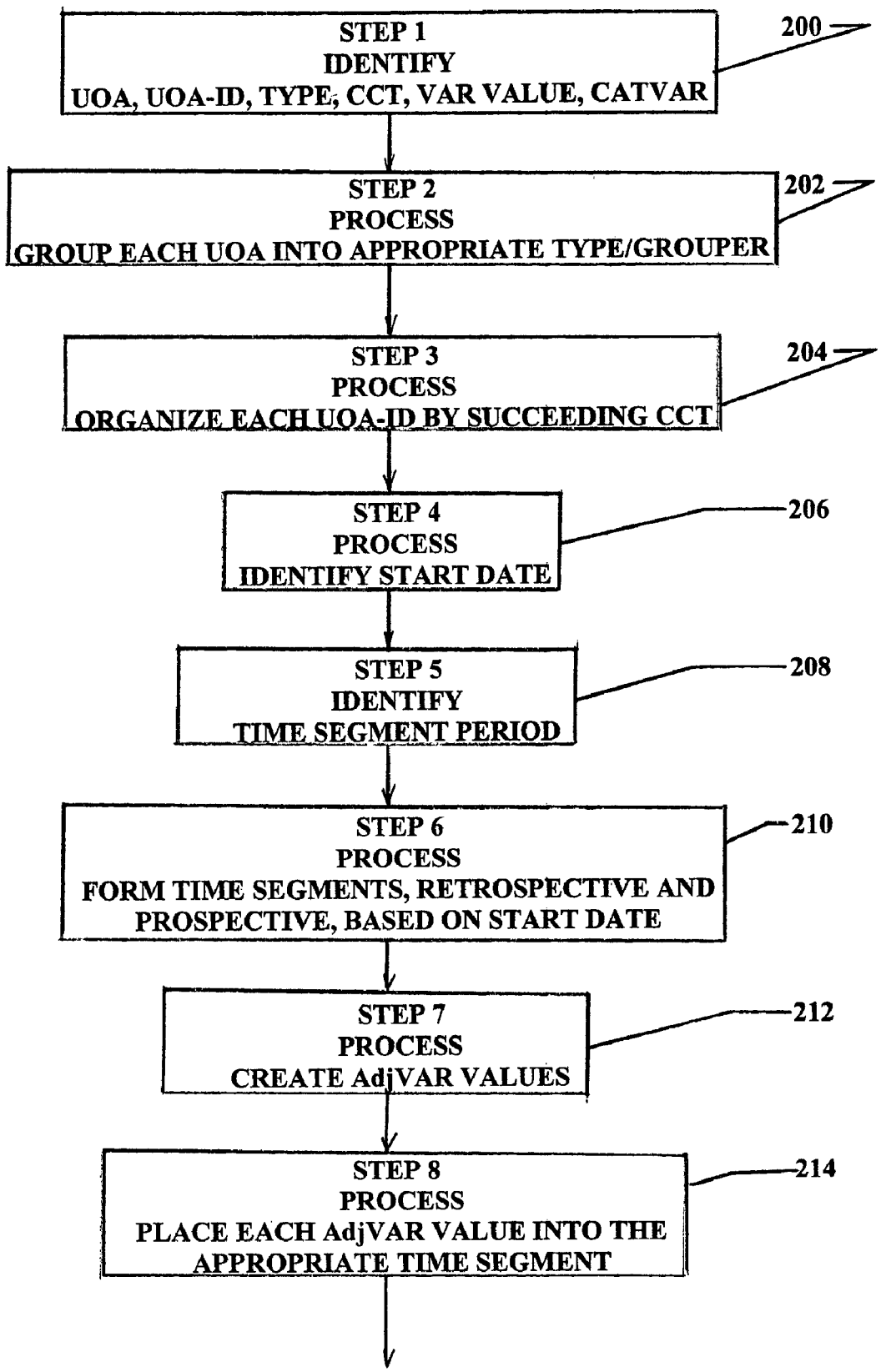

Referring to FIGS. 1, 2 and 3, a flowchart illustrating the overall structured methodology and design of the system software 104 of the present invention is shown. In a preferred embodiment of the invention, a set of information comprising the unit analysis ("UOA"), the identification of their particular UOA ("UOA-ID"), the Type, and the calendar clock date/time ("CCT") are identified (step 1) 200 by the system user (not shown) is stored in the information data bank, as represented by Table 1, within the memory 106 of the CPU 102. As used herein, the term "Unit of Analysis" means the basic or minimum analytical unit that is to be examined using the method and system of the present invention. The term "UOA-ID" means the particular individual UOA entity involved in the study. For example, in the retail industry, the UOA can be, but are not limited to, an individual person, an individual product line, individual type of person, store type or a section of a store, office type, etc. For the health care industry for example, the UOA can be, but are not limited to, patients having a common diagnosis or condition, medical offices, hospital units, hospitals, etc. Preferably, the UOA will be the most basic analytic unit that can be supported by the known information. The "UOA-ID" can include, but are not be limited to, an individual product, an individual person, an individual store, office, etc. For the health care industry for example, the UOA-ID can include, but are not limited to, an individual patient, medical office, hospital, or hospital unit. As used herein, the term "Type" means an event or action that operates as a trigger such that when the UOA-ID meets a given criteria it is included into a specific Population. Thus, "Type" refers specifically to the variable that will be used to direct the UOA-ID into a defined Population. For example, "Type" can include, but is not limited to, a specific diagnosis, or the performance of a specific procedure. CATVAR refers to "Categorical Variable" and can be of two types "fixed" or "dynamic." A fixed CATVAR (termed "CATVAR-F") is a variable associated with a UOA-ID that does not change over some designated CCT period. The duration of COT can be as wide as a lifetime (e.g. gender) or simply a CATVAR that does not likely change during the "Study Time" pf interest (i.e., the calendar (or clock) time of interest (e.g., the year 2110, Feb. 15 to Mar. 14, 1:00 A.M. to 1:15 A.M. on Apr. 3, 2001, etc.); an example would be the state of residence. A dynamic CATVAR 9termed VATVAR-D) is one that can take theoretically on different values per any given time segment. An example of this is filling a prescription in any given time segment, it could be filled or not filled.

As used herein, the term "Population" means a defined set comprising at least two or more UOA-IDs that meet an eligibility criteria (e.g. Type) selected for inclusion into the set.

TABLE 1

| STEP 1 INPUT INFORMATION | | | | | | |
| --- | --- | --- | --- | --- | --- | --- |
| UOA | UOA-ID | Type | VAR VALUE | CCT | CATVAR-F | CATVAR-D |
| Individual | 123 | A | 100 | 15JAN2000 | 1 | 1 |
| Individual | 123 | B | 200 | 01MAR2000 | 1 | 0 |
| Individual | 123 | D | 5000 | 15MAR2000 | 1 | 1 |
| Individual | 124 | C | 500 | 01APR2000 | 0 | 1 |

A Variable Value ("VAR Value") as well as CATVAR-F and CATVAR-D values are also inputted in step 1 200 by the user and is stored in the information data bank. As used herein, the "VAR Value" is a quantity variable or a value and can include, but is not limited to, a quantity count, a dollar value or economic value, the number of events, etc. As used herein, the CCT shall refer to the clock or calendar time at which the transaction of "VAR Value" takes place. The CATVAR are variables or variables per UOA-ID (or per UOA-ID & Time Segment) that are used to stratify the output expressions over the entire study time period or per time segment.

After entering the information in step 1 200, the user also identifies and enters the particular Type to be used to group each UOA. The system software 104 then operates (step 2) 202 to group each UOA-ID into an appropriate "Grouper" (This could be equivalent to a Type or could be derived from an algorithm that turns "many" into "few" which, as represented in Table 2, is then stored in separate Grouper "K" data files in the information data bank. "Grouper" algorithms that can be utilized by the software 104 to turn "many" into "few" are well known and can be proprietary, public, or custom built. For example, UOA-IDs, such as brands of like products (e.g. brands of toothpaste), can be grouped into a generic Grouper called "toothpaste." UOA-IDs, such as brands of cereal can be grouped into a generic Grouper called "cereal" or may be further grouped according to the size of the box of the cereal. In the health care industry, UOA-IDs, such as the 10,000+ codes used by health care providers on transaction/claim forms (ICD-9 codes) can be grouped into Groupers of genus and species type classification.

TABLE 2

STEP 2: GROUP EACH UOA-ID INTO APPROPRIATE GROUPER AND STORE INTO SEPARATE GROUPER "K" FILES

| UOA-ID | Type | CCT | Grouper |
|--------|------|-----------|---------|
| 123 | A | 15JAN2000 | X |
| 123 | B | 06FEB2000 | X |
| 124 | C | 01APR2000 | X |
| 123 | D | 10MAR2000 | Y |

Once the various Groupers have been formed, the software 104 operates to organize each UOA-ID, as represented by Table 3, within each Grouper "K" data file by succeeding CCT (step 3) 204 beginning with the earliest CCT thereby creating a virtual date field. The software 104 then operates to identify a "Start Time" which is the earliest CCT for each specific UOA-ID per Type (step 4) 206.

TABLE 3

STEP 4: IDENTIFY START TIME

| UOA-ID | Type | Start Time | Grouper |
|--------|------|------------|---------|
| 123 | A | 15JAN2000 | X |
| 124 | C | 01APR2000 | X |
| 123 | D | 01APR2000 | Y |

The user then selects and inputs a time segment period (step 5) 208 which the software 104 operates to form a plurality of time segments ("TS"), retrospective ("−") and prospective ("+"), based on the Start Time, as represented by Table 4, and each having some duration (step 6) 210. It should be understood that the duration can be of any length, e.g. based on days of the month which varies; however, preferably the duration is equal to the selected initial time segment period, also called the "Index Time Segment" as interpretation of findings may be easier. However, it may be more desirable in certain studies to use a calendar month, regardless of its duration, as a definition of a time segment. In that case, some cohort months would have UOA-IDs with "days" ranging from 28 to 31 days, as illustrated in tables 4-13.

TABLE 4

STEP 6: FORM TIME SEGMENTS FOR EACH UOA-ID (PROSPECTIVE + AND RETROSPECTIVE), BASED ON START TIME.

| UOA-ID | Type | Start Time | Grouper | TS − 2 | TS − 1 (Index) | TS + 1 | TS + 2 |
|--------|------|------------|---------|--------|----------------|--------|--------|
| 123 | A | 15JAN2000 | X | . | . | . | . |
| 124 | C | 01APR2000 | X | | . | . | . |
| 123 | D | 01APR2000 | Y | . | . | . | . |

Where "." = missing value
Where TS = 30 days in duration (only showing two TS prospectively ("+") and two TS retrospectively ("−"))

As shown, VAR Values that have been inputted and stored in the information data bank is then operated on by the system software 104 (step 7) 212 to mathematically adjust and standardized each VAR Value to create Adjusted Variable Values ("AdjVAR Values"), as represented by Table 5. For example, cost or purchase price of a product can be adjusted for inflation rates, premium pricing for a particular business plan, or any other adjustments deemed necessary by the user. It should be understood that the adjustment criterion is selected by the user and is important to enable the information to be properly compared.

TABLE 5

STEP 7: ADJUST AND STANDARDIZE EACH VAR VALUE TO CREATE AdjVAR VALUES

| UOA-ID | Type | AdjVAR VALUES* | CCT |
|--------|------|----------------|-----------|
| 123 | A | 100 | 15JAN2000 |
| 123 | B | 204 | 01MAR2000 |
| 123 | D | 5100 | 10MAR2000 |
| 124 | C | 515 | 01APR2000 |

Note:
Inflation adjusted to JANUARY2000 dollars (multiply VAR by adjustment per calendar month to derive AdjVAR Values).
JANUARY ADJUSTMENT = 1.0, FEBRUARY2000 = 1.01, MARCH2000 = 1.02, APRIL2000 = 1.03

The AdjVAR Values are then stored (step 8) 214 in the information data bank for the appropriate time segment, as represented by Table 5. In this way, VAR Values are changed from being tracked by calendar time to Cohort Time. As used herein "Cohort Time" means that the Start Time is based on a defining event, which is the last date/clock time that the individual UOA-ID meets all of the eligibility criteria to be included into the population. Thus, in Cohort Time, the start of TS+1 (Index month) will be the date or time all of the eligibility criteria is met per UOA-ID, not the calendar date or time the resource optimizing study begins. For example, an individual ("first individual") who became eligible for a study on Jan. 1, 2001 and participated until Dec. 31, 2001 would have one year of participation. Another individual ("second individual") who started on Dec. 1, 2001 would have one month of experience during the study time from Jan. 1, 2001 to Dec. 31, 2001. In a month-based Cohort Time, the first individual first month would be Jan. 1-31, 2001, and the second individual's first month would be Dec. 1-31, 2001. Thus, in Cohort Time, however, both individuals would be counted in month 1, however, in months 2 to 12, the first individual would be counted while the second individual would not be counted.

After the AdjVAR Values have been sorted and placed in appropriate time segments in step 8 314, as represented in Table 6, the process (steps 1-8) is repeated (step 9) 216 for each UOA-ID.

TABLE 6

STEP 8: Sort and place each AdjVAR for each UOA-ID into the appropriate Time Segment (TS)

| UOA-ID | Type | Start Time | Grouper | TS − 2 | TS − 1 | TS + 1 | TS + 2 |
|---|---|---|---|---|---|---|---|
| 123 | A | 15JAN2000 | X | . | . | 100 | 5100 |
| 124 | C | 01APR2000 | X | . | . | 515 | . |
| 123 | D | 01APR2000 | Y | 100 | 5100 | . | . |

After step 9 216 is complete, eligibility scores (Potential Eligibility Scores and Actual Eligibility Scores), prospective and retrospective, are then calculated (step 10) 218. As used herein, Potential Eligibility Scores (retrospective [PRES] and prospective [PPES]), are used to help depict "lost to follow-up" findings when methodology like "intent to treat" is utilized and are based on the "Study Time," i.e., the calendar (or clock) time of interest (e.g., the year 2110, Feb. 15 to Mar. 14, 1:00 A.M. to 1:15 A.M. on Apr. 3, 2001, etc.). Since some of the UOA-IDs may not be potentially eligible for the entire study time period, a score is given for each UOA-ID both prospectively and retrospectively. For example, the first individual in the above example "started" on January 1, which was also the first day of the study, a study which operationally ended Dec. 31, 2001. Accordingly, the individual's prospective Potential Eligibility Score is 12 Cohort months out of a possible 12 Cohort months (equivalent in this case to the 12 calendar months of the study). However, the individual's retrospective Potential Eligibility Score is based upon zero (0) retrospective Cohort months out of a possible 12 retrospective Cohort months (this score is 12 because any UOA-ID could have "started" on Dec. 31, 2001 and would therefore would be a maximum or potential 12 month period of time before onset) as there is no "potential" information available for the first individual prior to Jan. 1, 2001 (e.g. the individual's potential score is 12 divided by 12 and the individual's retrospective score is 0 divided by 12, which will default to zero by the algorithm). The second individual who "started" on Dec. 1, 2001 has one prospective Cohort month out of a possible 12 Cohort months of prospective eligibility so the individual's prospective Potential Eligibility Score is a function of 1 out of 12 (e.g. 1 divided by 12). The individual's retrospective Potential Eligibility Score is a function of 11 out of 12 (e.g. 11 divided by 12) as there is a potential of having 11 months of information on that individual (from Jan. 1, 2001 to Nov. 30, 2001) when the individual was not a member of the defined Population. Retrospective data can be used in estimating "predictors" of becoming a member of a defined population, can be used to understand trends prior to becoming a member of a Population, etc. However, it is not necessary that UOA-IDs have both retrospective and prospective time segments. In fact, in two examples below all UOA-IDs have only prospective time segments. An example showing the potential eligibility scores are shown in Tables 7 and 8.

TABLE 7

| UOA-ID | Type | Start Time | Grouper | PTS + 1 | PTS + 2 | PTS + 3 | PTS + 4 | PTS + 5 | PTS + 6 |
|---|---|---|---|---|---|---|---|---|---|
| 123 | A | 15JAN2000 | X | 1.0 | 1.0 | 1.0 | 1.0 | 1.0 | 1.0 |
| 124 | C | 01APR2000 | X | 1.0 | 1.0 | 1.0 | 1.0 | 1.0 | 1.0 |

| UOA-ID | Type | Start Time | Grouper | PTS + 7 | PTS + 8 | PTS + 9 | PTS + 10 | PTS + 11 | PTS + 12 |
|---|---|---|---|---|---|---|---|---|---|
| 123 | A | 15JAN2000 | X | 1.0 | 1.0 | 1.0 | 1.0 | 1.0 | 0.5 |
| 124 | C | 01APR2000 | X | 1.0 | 1.0 | 1.0 | 0.0 | 0.0 | 0.0 |

| UOA-ID | Type | Start Time | Grouper | PTS − 6 | PTS − 5 | PTS − 4 | PTS − 3 | PTS − 2 | PTS − 1 |
|---|---|---|---|---|---|---|---|---|---|
| 123 | A | 15JAN2000 | X | 0.0 | 0.0 | 0.0 | 0.0 | 0.0 | 0.5 |
| 124 | C | 01APR2000 | X | 0.0 | 0.0 | 0.0 | 1.0 | 1.0 | 1.0 |

| UOA-ID | Type | Start Time | Grouper | PTS − 12 | PTS − 11 | PTS − 10 | PTS − 9 | PTS − 8 | PTS − 7 |
|---|---|---|---|---|---|---|---|---|---|
| 123 | A | 15JAN2000 | X | 0.0 | 0.0 | 0.0 | 0.0 | 0.0 | 0.0 |
| 124 | C | 01APR2000 | X | 0.0 | 0.0 | 0.0 | 0.0 | 0.0 | 0.0 |

TABLE 8

| UOA-ID | Type | Start Time | Grouper | PPES | PRES |
|---|---|---|---|---|---|
| 123 | A | 15JAN2000 | X | 11.5 | 0.5 |
| 124 | C | 01APR2000 | X | 9.0 | 3.0 |
| 123 | D | 10MAR2000 | Y | 9.33 | 2.66 |

Key: PPES = Potential Prospective Eligibility Score (sum of PTS + values), PRES = Potential Retrospective Eligibility Score (sum of PTS values)

As used herein, the "Actual Eligibility Score" is the proportion of each time segment that the UOA-ID was eligible to be a member of a specific Population. For example, if the time segment comprises 30 days and the UOA-ID was eligible to be in the Population for 15 days of that time segment, the Actual Eligibility Score would be 0.5. If the UOA-ID were eligible to be in the Population for the entire 30 days of a time segment, the Actual Eligibility Score would be 1.0. It should be understood that if there were no information for the UOA-ID for a particular time segment, the Actual Eligibility Score would be assigned the value of "missing." As will be seen later herein, by assigning the value of "missing" takes the UOA-ID out of the study for that particular time segment thereby eliminating any inaccurate biasing of the data. An example showing the Actual Eligibility Scores are shown in Tables 9 and 10.

TABLE 9

| | Input | |
|---|---|---|
| UOA-ID | Eligibility Start | Eligibility End |
| 123 | 01JAN1999 | 31MAR2000 |
| 123 | 01APR2000 | 31DEC2000 |
| 124 | 01APR2000 | 01JUN2000 |

TABLE 10

| UOA-ID | Type | Start Time | Grouper | TS − 2 | TS − 1 | TS + 1 | TS + 2 |
|---|---|---|---|---|---|---|---|
| 123 | A | 15JAN2000 | X | . | 0.5 | 1.0 | 1.0 |
| 124 | C | 01APR2000 | X | . | . | 1.0 | 1.0 |

Using the Actual Eligibility Score, as illustrated in Tables 11, 12 and 13, the AdjVAR Value is adjusted again with respect to eligibility by performing the appropriate mathematical function for each time segment (step 10) 218 to generate an Eligible Adjusted Variable Value ("EAV") for the time segment. It should be understood that the EAV, as used herein, is expressed by the same units as used for the VAR Value. Further, for any UOA-ID that is eligible (actual) for any given time segment, if there is no VAR Value ("missing") the UOA-ID would be assigned a value of "0." Thus, EAV may be, but are not limited to, a quantity count, dollar value, number of products, and number of events, etc.

TABLE 11

Input (AdjVAR per TS FROM STEP 9)

| UOA-ID | Type | Start Time | Grouper | TS − 2 | TS − 1 | TS + 1 | TS + 2 |
|---|---|---|---|---|---|---|---|
| 123 | A | 15JAN2000 | X | . | . | 100 | 5100 |
| 124 | C | 01APR2000 | X | . | . | 515 | . |

TABLE 12

Input (Actual Eligibility per TS FROM STEP 10)

| UOA-ID | Type | Start Time | Grouper | TS − 2 | TS − 1 | TS + 1 | TS + 2 |
|---|---|---|---|---|---|---|---|
| 123 | A | 15JAN2000 | X | . | . | 0.5 | 1.0 |
| 124 | C | 01APR2000 | X | . | . | 1.0 | 1.0 |

TABLE 13

Output:

| UOA-ID | Type | Start Time | Grouper | EAV − 2 | EAV − 1 | EAV + 1 | EAV + 2 |
|---|---|---|---|---|---|---|---|
| 123 | A | 15JAN2000 | X | . | . | 200 | 5100 |
| 124 | C | 01APR2000 | X | . | . | 515 | 0 |

Key: EAV = Eligiblity adjusted AdjVAR

After the Software has calculated the EAV the software operates (step 12) 222 to prepare an aggregate or Summary Metric for all the UOA-ID's in a time segment. For example, for a given time segment, the average, medium, etc. EAV may be calculated. The Summary Metric is then used, together with the various inputs and derived parameters, to calculate an Output Expression. It should be understood to those skilled in the art that the Output Expression can be in the form of a display, such as, but not limited to, a video, printed matter, projected image, or a recorded display, which can then be used for analyzing, evaluating and optimizing resource allocation.

As used herein, the Output Expression is any representation that can show a relationship between one or more of the Summary Metrics, and the inputs and derived parameters and may be generated using various techniques. In a preferred embodiment of the invention, the Output Expression is in the form of a graphic representation, table or a chart.

In order to better illustrate the method and system for optimizing resource allocation, the following example is provided:

The present invention provides a method and a system for implementing the method of identifying and optimizing resource allocation in the health care industry. As used in this example, optimization of resource allocation includes evaluating where to allocate current resources for the purpose of obtaining a desired outcome, such as reducing excessive costs due to over utilization or resources, as well as assessing the impact that such the resources had on the resulting outcome. Unfortunately, until now the current metric systems typically used in the health care industry operate to compute costs over large time periods (e.g. a calendar year) in defined populations and fail to account for changes in cost patterns in certain patient Populations within these large time segments.

The transaction of this example is initiated by the interaction between a health care provider and a patient where the Type (e.g. diagnosis or product) is "purchased" on a specific date and/or time (CCT). Coupled with eligibility to experience a transaction, the method and system for utilizing the method of the present invention transforms these data into Cohort time trends of utilization (e.g. cost) per Type. These trends are then used to 1) better understand current trends in Cohort Time, and 2) to better estimate resource allocation to meet specific goals of improving utilization over Cohort Time or CCT.

For this example, the UOAs are specific patients within a defined Population and the UOA-ID is a unique individual who meets the criteria for a defined Population based on Type (or Types). Type shall be a diagnosis, drug, code (based for example on ICD9), etc. The CCT shall be the calendar or clock time of the transaction. VAR Value shall be the amount of the transaction or some numeric value.

Table 14 illustrates the method of the present invention in accordance with example 1.

TABLE 14

| STEPS | Health Care Example |
|---|---|
| 1 | Identify each UOA (patients within a defined Population), UOA-ID (a specific patient), Type (a diagnosis, drug, code, etc.), CCT (time of the transaction), CATVAR (categorical variable) VAR Value (amount of transaction) |
| 2 | Group each UOA-ID into appropriate Groupers and store into separate "K" files. The "Grouper" takes many "Types" (e.g. diagnoses) codes and creates a new "Grouper" variable." Separate into data set per each Grouper. |
| 3 | Organize each UOA-ID within each Grouper "K" file by succeessing CCT. |
| 4 | Select the earliest Start Time per UOA-ID |
| 5 | Input length of time segment period(s). For example, 30 days. |
| 6 | Form time segments, retrospective and prospective, based on the Start Time. The time segments are based upon time before and after the Start Time in 30 day increments. |

TABLE 14-continued

| STEPS | Health Care Example |
|---|---|
| 7 | Adjust and standardize each VAR Value to create AdjVAR Values. In this example VAR Value (e.g., $) is influenced by calendar time (e.g. inflation). |
| 8 | Sort and place AdjVAR Values into appropriate time segments based upon a match of the time of the AdjVAR Value transaction. |
| 9 | Repeat steps 1-8 for each UOA-ID |
| 10 | Calculate an Eligibility Score (potential and actual) prospective and retrospective for each UOA-ID. Based upon calendar or clock time of study each UOA-ID receives a potential score. Based upon the actual eligibility during each time segment each UOA-ID receives an Actual Eligibility Score per time segment |
| 11 | Calculate the Adjusted variable Value (EAV) for each time segment. Mathematical Operation (situation specific). In this example the AdjVAR is divided by the Actual Eligibility Score to generate an EAV. The assumption that was made in this example is that if the UOA-ID had been eligible it would have had a similar AdjVAR Value across the entire time period. If proportion eligibility was 0.5 and AdjVAR Value was $100, then the EAV would be $200.00. The assumption is that if an UOA-ID had been eligible the entire month one needs to know the expected value. The Potential Eligibility score should be merged with the EAV for proper interpretation of Output Expression |
| 12 | Generate an Output Expression. From this step, the "average" (or other summary metric) of one defined Population can be trended per time segment (30 days) and compared to the trend of the percent of other populations (or sub-sets per Population based upon other Types and/or other variables, e.g. age, sex, etc). A dichotomous variable (DV) is calculated from "threshold value" (e.g. $99^{th}$ percentile of costs) and the Population is trended over time segment based upon the percent of the Population above the threshold |
| 13 | Stratify the Output Expression. The Output Expression of the "average" or the "DV" can be stratified by a CATVAR that is fixed or by one that is dynamic (a two step process) creating two or more output expressions. These output expression should be compared to determine a) which is the most optimal population on which to intervention or b) which is the most optimal intervention. |

The term "Health care" has a wide range of meanings. It should be understood that method and system for performing the method of the present invention could be used for different purposes and different functions. For example, it can be used by the "payers" (Health care insurance, employer, government, etc.), "providers" (e.g. hospitals, physicians, nursing homes, etc.) disease management functions, utilization management, case management, concurrent review, actuarial pricing, health economics, and the evaluation of "technology" including pharmaceuticals and durable medical goods and devices (i.e., "technology assessment").

In order to illustrate the various Output Expressions that can be generated using the method and the system of the present invention, FIGS. 3 through 6 and associated descriptions are used and should not be construed to define or bound the present invention. It should be understood that the values shown in Tables 17-22 are for illustrative purposes only.

Figure 4:
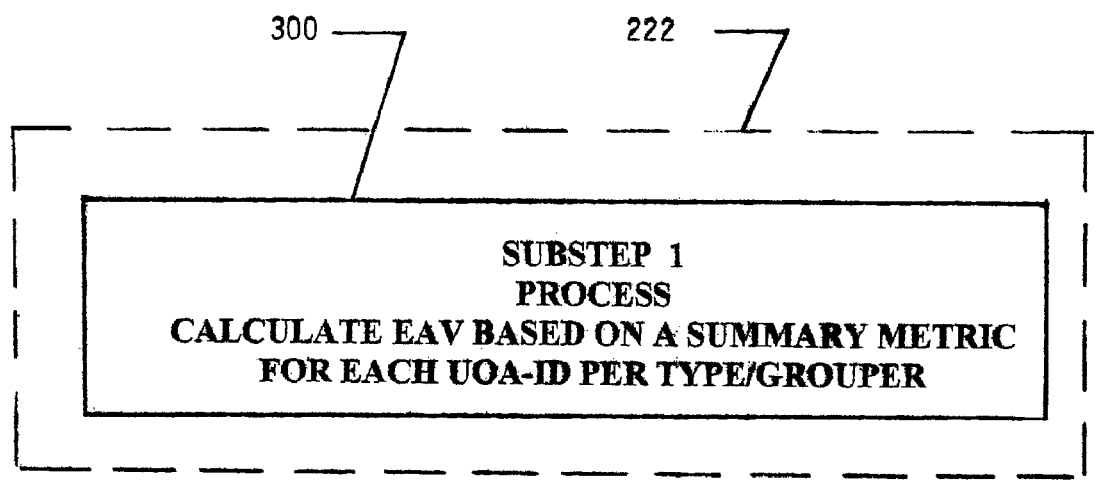
FIG. 4 is a flow diagram illustrating the various functional steps for generating a first typical Output Expression showing an EAV trend based on a selected summary metric.

Referring to FIGS. 3 and 4 is a flow diagram illustrating in more detail step 12 222 of the method of generating a first typical Output Expression. In this example, as shown in Table 4, the Output Expression generated in substep 1 300 is an EAV trend that is based on a selected summary metric (e.g.

mean, median, average, etc.) for all UOA-IDs per Type or Grouper for each time segment. As used herein, the Index Time Segment is the initial or "Start Time" as previously defined and only prospective time segments are shown. At this point, CATVAR-F or CATVAR-D (collectively referred to as "CATVAR") should be used to stratify the original tables of the defined population.

TABLE 15

| Time Segment (TS) | EAV Summary Metric |
|---|---|
| TS + 1 (Index) | $2,656.76 |
| TS + 2 | $525.81 |
| TS + 3 | $548.19 |
| TS + 4 | $533.17 |
| TS + 5 | $416.15 |
| TS + 6 | $304.30 |

TABLE 15A

| Time Segment (TS) | CATVAR = 1 EAV Summary Metric | CATVAR = 0 EAV Summary Metric |
|---|---|---|
| TS + 1 (Index) | $1328.38 | $3,985.14 |
| TS + 2 | $262.91 | $788.72 |
| TS + 3 | $274.10 | $822.29 |
| TS + 4 | $266.59 | $799.76 |
| TS + 5 | $208.08 | $624.23 |
| TS + 6 | $152.15 | $456.45 |

Figure 5:
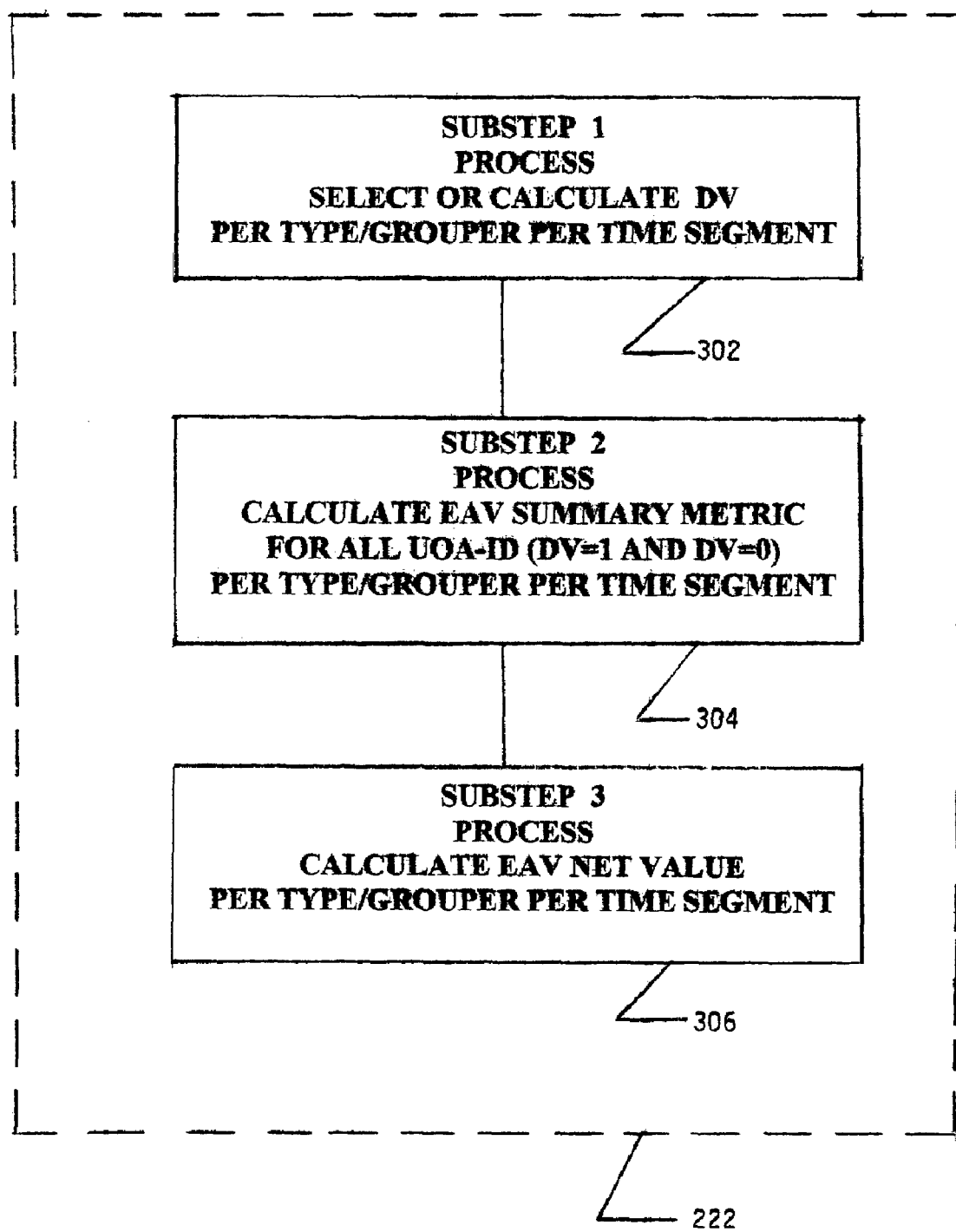
FIG. 5 is a flow diagram illustrating the various functional steps for generating another typical Output Expression showing an EAV Net Value Summary Metric based on a dichotomous variable.

Referring to FIGS. 3 and 5 is a flow diagram illustrating in more detail step 12 222 of the method of generating a typical Output Expression. Another typical Output Expression that can be generated by the method and system of the present invention is shown and comprises an EAV summary metric trend in dichotomous variable form (i.e. a variable with values of "0" and "1") per Type/Grouper per time segment. Depending on the particular study, the DV can be either a "1" or a "0." The DV can also be calculated based on a selected or calculated threshold EAV value (such as in the previous health care Example 1) whereby the EAV is placed into dichotomous variable form by determining when the VAR Value for a UOA-ID exceeds a specified threshold value, if it does the UOA-ID would be given a DV equal to "1", if not the DV would be "0". As used herein, the "threshold value" is an arbitrary cost provided by the user. This cost could be but not limited to, the amount currently being spent in a program, target costs, or some other value of importance to the user.

As shown in FIG. 5 and illustrated in Table 15 and Table 15A, step 12 222 of the method of the present invention includes substep 1 302 of selecting or calculating a DV per Type/Grouper per time segment. For example, as shown in Table 5, for TS+1 (Index), 37.6% of UOA-Ids received a DV equal to "1." Table 16A shows the entire defined population subdivided by a two category variable, thus, TS+1 of CATVAR=1 is 18.8% and TS+1 of CATVAR=0 is much larger at 56.3%.

TABLE 16

| Time Segment (TS) | Percent Dichotomous Variable [DV = 1/ (DV = 1 + DV = 0) * 100] |
|---|---|
| TS + 1 (Index) | 37.6 |
| TS + 2 | 8.4 |
| TS + 3 | 8.1 |
| TS + 4 | 6.2 |
| TS + 5 | 6.6 |
| TS + 6 | 3.1 |

TABLE 16A

| Time Segment (TS) | CATVAR = 1 Percent Dichotomous Variable [DV = 1/ (DV = 1 + DV = 0) * 100] | CATVAR = 0 Percent Dichotomous Variable [DV = 1/ (DV = 1 + DV = 0) * 100] |
|---|---|---|
| TS + 1 (Index) | 18.8 | 56.3 |
| TS + 2 | 4.2 | 16.8 |
| TS + 3 | 4.0 | 16.2 |
| TS + 4 | 3.1 | 12.4 |
| TS + 5 | 3.3 | 13.2 |
| TS + 6 | 1.6 | 6.2 |

After completing substep 1 302, as illustrated in Table 17, the EAV summary metric is calculated using Tables 4 and 5, substep 2 304, for all UOD-IDs with a DV of "1" and for a DV of "0" per Type/Grouper per time segment. For example, for TS+1 (Index) 37.6% UOA-Ids had an EAV Summary Metric of $6,953.00 and 62.4% UOA-Ids have an EAV Summary Metric of $68.00. This metric is further subdivided by the two value CATVAR in Table 17A. Table 18 subdivided by CATVAR shows the difference between EAV summary metrics among those with DV=1 vs DV=0. This difference is used to calculate the estimate "cash value" of changing the status of a UOA-ID that is expected to be DV=1 to DV=0 or vica versa.

TABLE 17

| Time Segment (TS) | EAV Summary Metric (Where DV = 1) | EAV Summary Metric (Where DV = 0) |
|---|---|---|
| TS + 1 (Index) | $6,953 | $68 |
| TS + 2 | 5,649 | 56 |
| TS + 3 | 6,087 | 60 |
| TS + 4 | 7,480 | 74 |
| TS + 5 | 5,527 | 55 |
| TS + 6 | 7,503 | 74 |

TABLE 17A

| Time Segment (TS) | CARVAR = 1 EAV Summary Metric (Where DV = 1) | CATVAR = 1 EAV Summary Metric (Where DV = 0) | CATVAR = 0 EAV Summary Metric (Where DV = 0) | CATVAR = 0 EAV Summary Metric (Where DV = 0) |
|---|---|---|---|---|
| TS + 1(Index) | $6,953 | $68 | 10,429 | $74 |
| TS + 2 | 2,824 | 56 | 8,473 | 55 |
| TS + 3 | 3,043 | 60 | 9103 | 60 |
| TS + 4 | 3,740 | 74 | 11,220 | 74 |
| TS + 5 | 2,763 | 55 | 8,290 | 56 |
| TS + 6 | 3,751 | 74 | 11,254 | 68 |

The EAV Net Value per Type/Grouper per Time Segment is then calculated, substep 3 306. As used herein, as illustrated in Table 18, the EAV Net Value is the difference in EAV between a DV equal to "1" to the DV equal to "0", or vice versa.

TABLE 18

| Time Segment (TS) | CATVAR = 1 EAV Net Value (DV = 1 − DV = 0) | CATVAR = 0 EAV Net Value (DV = 1 − DV = 0) |
|---|---|---|
| TS + 1 (Index) | 6,885 | 10,355 |
| TS + 2 | 2,768 | 8,418 |
| TS + 3 | 2,983 | 9,043 |
| TS + 4 | 3,666 | 11,146 |
| TS + 5 | 2,708 | 8,234 |
| TS + 6 | 3,677 | 11,186 |

Figure 6:
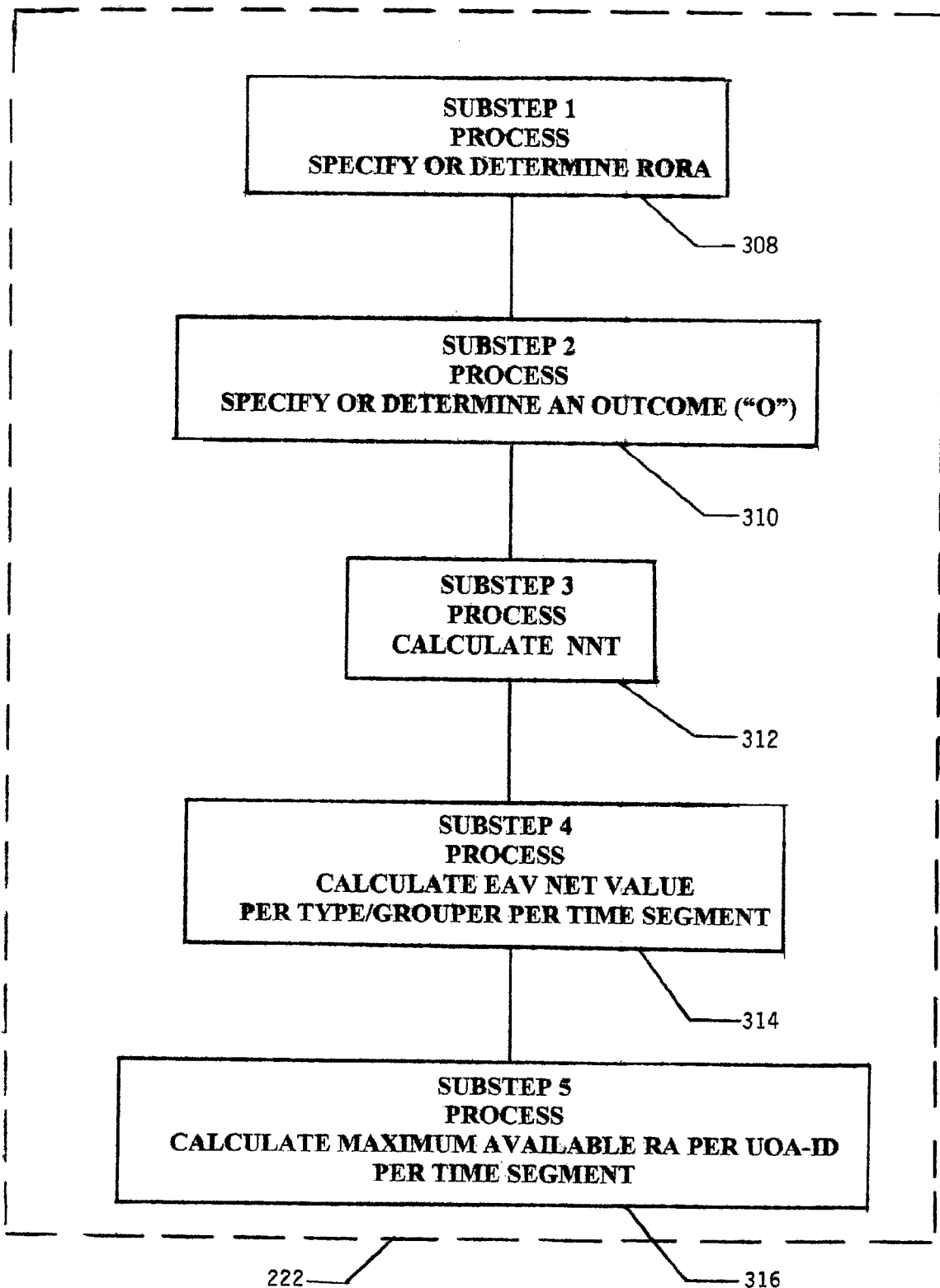
FIG. 6 is a flow diagram illustrating the various functional steps for generating another typical Output Expression showing available Resource Allocation.

Referring to FIGS. 3 and 6 is a flow diagram illustrating in more detail step 12 222 of the method of generating a typical Output Expression. Another typical Output Expression that can be generated by the method and system of the present invention comprises a showing of the maximum available resource allocation ("RA") per time segment.

As illustrated in Table 19, step 12 222 of the method of the present invention includes substep 1 308 of specifying or determining a return on resource allocation ("RORA"). segment. In this specific example, the RORA is selected to be 1.0 that represents the RORA break-even point that is the same for CATVAR=0 and CATVAR=1.

TABLE 19

| Time Segment (TS) | CATVAR = 1 Return on Resource Allocation (RORA) | CATVAR = 0 Return on Resource Allocation (RORA) |
|---|---|---|
| TS + 1 (Index) | 1.0 | 1.0 |
| TS + 2 | 1.0 | 1.0 |
| TS + 3 | 1.0 | 1.0 |
| TS + 4 | 1.0 | 1.0 |
| TS + 5 | 1.0 | 1.0 |
| TS + 6 | 1.0 | 1.0 |

After completing substep 1 308, an Outcome ("O"), as illustrated in Table 20 and Table 20A (subdivided by CATVAR), is specified by the user substep 2 310. As used herein the "Outcome" is the expected change in percentage of DV equal to "1" per time segment (For example, between "old" and "new" EAVs per time segment). As used in this case, a change of 10% in the percent of the DV (as shown in Table 16) is desired. In TS+1(Index), a 10% change of 37.6% would be 3.76 percentage points or an expected 33.84 percent DV (37.6−3.76=33.84).

TABLE 20

| Time Segment (TS) | Expected Change |
|---|---|
| TS + 1 (Index) | 10% |
| TS + 2 | 10% |
| TS + 3 | 10% |
| TS + 4 | 10% |
| TS + 5 | 10% |
| TS + 6 | 10% |

TABLE 20A

| Time Segment (TS) | CATVAR = 1 Expected Change | CATVAR = 0 Expected Change |
|---|---|---|
| TS + 1 (Index) | 10% | 10% |
| TS + 2 | 10% | 10% |
| TS + 3 | 10% | 10% |
| TS + 4 | 10% | 10% |
| TS + 5 | 10% | 10% |
| TS + 6 | 10% | 10% |

The number needed to target ("NNT") to impact one UOA-ID per time segment is then calculated in substep 3 312. For example, for a total Population being equal to 100%, the percentage of Population with a DV equals to "1" is determined. The user can then specify the desired Outcome ("O"), such as 10%, and the NNT is calculated, as illustrated in Table 21, by dividing the total Population by the percentage of the population where the DV is equal to "1" and further dividing by the desired Outcome (NNT=(Total Population/Percentage of Population with a DV equal to "1")/Outcome). Table 21A (CATVAR=1) and Table 21B (CATVAR=2) show the NNT per respective CATVAR.

TABLE 21

| Time Segment (TS) | Formula (substep 3) | NNT (Number Needed to Treat)* |
|---|---|---|
| TS + 1 (index) | (100/37.6)/10 | 27 |
| TS + 2 | (100/8.4)/10 | 119 |
| TS + 3 | (100/8.1)/10 | 123 |
| TS + 4 | (100/6.2)/10 | 161 |
| TS + 5 | (100/6.6)/10 | 152 |
| TS + 6 | (100/3.1)/10 | 323 |

*NNT is rounded to an integer in this example.

TABLE 21A

| | (CATVAR = 1) | |
|---|---|---|
| Time Segment (TS) | Formula (substep 3) | NNT (Number Needed to Treat)* |
| TS + 1 (index) | (100/18.8)/10 | 53 |
| TS + 2 | (100/4.2)/10 | 238 |
| TS + 3 | (100/4.0)/10 | 250 |
| TS + 4 | (100/3.1)/10 | 323 |
| TS + 5 | (100/3.3)/10 | 303 |
| TS + 6 | (100/1.6)/10 | 625 |

TABLE 21B

| | (CATVAR = 0) | |
|---|---|---|
| Time Segment (TS) | Formula (substep 3) | NNT (Number Needed to Treat)* |
| TS + 1 (index) | (100/56.3)/10 | 18 |
| TS + 2 | (100/16.8)/10 | 60 |
| TS + 3 | (100/16.2)/10 | 62 |
| TS + 4 | (100/12.4)/10 | 81 |
| TS + 5 | (100/13.2)/10 | 76 |
| TS + 6 | (100/6.2)/10 | 161 |

The EAV Net Value is then calculated in substep 4 314 and is then used to calculate the maximum available resource allocation ("RA") per UOA-ID per time segment substep 5 316. Available resource allocation ("RA") is calculated, as illustrated in Table 23, by dividing the EAV Net Value by the number needed to target ("NNT") which was previously calculated in substep 3, 310 (RA=O/RORA).

TABLE 22

| Time Segment (TS) | Formula* | RA |
|---|---|---|
| TS + 1 (index) | ($6,885/27)/1.0 | $255 |
| TS + 2 | ($5,593/119)/1.0 | $47 |
| TS + 3 | ($6,027/123)/1.0 | $49 |
| TS + 4 | ($7,406/161)/1.0 | $46 |
| TS + 5 | ($5,472/152)/1.0 | $36 |
| TS + 6 | ($7,429/323)/1.0 | $23 |

*(EAV Net Value/NNT)/RORA = RA. The integer value of NNT from Table 21 was used here
**NNT is based on the rounded value as an integer.

TABLE 22A

| | CATVAR = 1 | |
|---|---|---|
| Time Segment (TS) | Formula* | RA |
| TS + 1 (index) | ($6,885/53)/1.0 | $129.90 |
| TS + 2 | (2,768/238)/1.0 | 11.63 |
| TS + 3 | (2,983/250)/1.0 | 11.93 |
| TS + 4 | (3,666/323)/1.0 | 11.34 |
| TS + 5 | (2,708/303)/1.0 | 8.94 |
| TS + 6 | (3,677/625)/1.0 | 5.88 |

TABLE 22B

| | CATVAR = 0 | |
|---|---|---|
| Time Segment (TS) | Formula* | RA |
| TS + 1 (index) | ($10,335/18)/1.0 | $574 |
| TS + 2 | (8,414/60)/1.0 | 140 |
| TS + 3 | (9,043/62)/1.0 | 146 |
| TS + 4 | (11,146/81)/1.0 | 138 |
| TS + 5 | (8,234/76)/1.0 | 108 |
| TS + 6 | (11,186/161)/1.0 | 70 |

It should now be apparent that with all of the various Output Expressions, the Cohort Time trend calculated per group (or sub-group) can be compared to other groups (or sub-groups). This can be based on Type or another variable and can be used to determine Resource Allocation ("RA"), Output ("O"), and Return on Resource Allocation ("RORA") per these sub-groups/Types and per CATVAR. Referring to FIG. 3B, once the desired Output Expression has been generated (step 12), the CATVAR can be used to stratify any Output Expression (step 130) 223 as illustrated in FIG. 7. It should also now be apparent to those skilled in the art that as shown from the above description the RA, RORA, and the Output are related mathematically. Accordingly, where two of such values are known, the third can be easily calculated using simple algebra. Thus the method can be used to calculate estimates such as "return on investment" (RORA in the terminology used here) when the outcome and the resources allocated are known. Moreover, if RORA and RA are known, the outcome can be estimated. The latter is useful when comparing the impact of a certain resource allocation decision on one population, compared to another resource allocation decision on another comparable (e.g., both selected by randomization) Population.

This grouping stratification can be based on variables (including Type) that are derived from inputted variables in the Index Time segment only, other time segment only, or all time segments. For example:

1) A "count" (the number of times an UOA-ID is above the threshold). For example if there were four time segments, any UOA-ID could have the "count" value of 0, 1, 2, 3, or 4) can be used. This "count" variable can become a stratifying variable to determine RORA, RA, or O per time segment.
2) The trend of the UOA-IDs above some threshold value in the Index Month can be calculated to determine the percentage of this sub-population (a) above the threshold in other months (prospective or retrospective) and/or (b) below the threshold in other months.
3) The trend of the UOA-IDs that are not above some threshold in the Index Month can be calculated to determine the percentage of this sub-population that (a) continue at or below the threshold in other months or (b) that change status to the group above the threshold in other months.
4) The trends of No. 2 and No. 3 can be calculated beginning the analysis in a month other than the Index Month (this can be valuable when the data is not immediately available and potential actions to change trends will only occur in time segments other than the Index Time Segment).
5) Using an additional variable (e.g., where an UOA-ID has evidence of another "Type" in either the Index Month or other months). Subdivide the Population by those with this additional "Type" and those without this additional "Type" and calculate trends and RA, O, and RORA as needed.

6) Using any additional CATVAR variable (other than Type) that is included in some set of information (that can be linked to a UOA-ID) any time segment, this can be fixed (e.g. sex) or variable (e.g., sales per month), and stratify by this variable, calculating trends, and RA, O, and RORA.

It should be now be apparent to those skilled in the art that these Cohort Time calculations can be easily translated back into CCT for financial budgeting and reporting. This can be accomplished by inclusion of the "Start Time" CCT into data set per UOA-ID by Type/Grouper. That is, using the resources allocation estimates per cohort time segment, these time segment specific estimates can be place back into CCT to estimate resources allocated per CCT time segment. This is accomplished by maintaining the start CCT per UOA-ID in the set of information. See Table 23 for example the simple method of transforming Cohort Time values for budgeting per calendar time. It should be understood that Table 23 can be subdivided into 2 or more tables based on CATVAR as well.

determines per UOA-ID which time segments (both prospective and retrospective) have the potential to have VAR Values in them. This is a function of Start Time in which each UOA-ID entered the Population and the range of CCT of the study time. The actual eligibility score is based upon the Start Time in which the UOA-ID entered the Population and is calculated based on the UOA-ID. A "missing" value in VAR Value during a time segment can mean either the UOA-ID was eligible and had no VAR Value or that the UOA-ID was not potentially eligible and the UOA-ID had no VAR Value. The VAR Value and the eligibility scores can then be merged to calculate an EAV. The EAVs can be summarized across all the UOA-IDs to enable one to estimate resources that can be allocated per UOA-ID per Cohort time segment to reach a defined outcome based on a defined return on resource allocation estimate and that can be subdivided by CATVAR.

It has been found and should be understood to those skilled in the art that the method and the system for performing the

TABLE 23

| Distribution per Calendar Time Segment (equal in duration to Cohort TS) | DV = 1 (expected percentage) | DV = 0 (expected percentage) | Total (expected percentage) | RA ESTIMATES (per UOA-ID)* |
|---|---|---|---|---|
| TS + 1 (index TS) | 37.6% | 62.4% | 100.0 | $255 |
| TS + 2 | 8.4 | 91.6 | 100.0 | $47 |
| TS + 3 | 8.1 | 91.9 | 100.0 | $49 |
| TS + 4 | 6.2 | 93.8 | 100.0 | $46 |
| TS + 5 | 6.6 | 93.4 | 100.0 | $36 |
| TS + 6 | 3.1 | 96.9 | 100.0 | $23 |
| Column Sum/ Number of Cohort Time Segment | 69.99%/6 | 529.99%/6 | 600/6 | $456/6 |
| Budget Estimates (Column Average) | 11.67% | 88.33% | 100.0% | $76 |

Key to table: *Resource Allocation (RA) Estimates (where Outcome expectation = 10% and Return on Resource Allocation = 1.0) The calculations are based on a equal weighting of UOA-ID per Cohort time segment. Thus (100/6 or 16.66%) of the total Population during any calendar time segment is in any of the six Cohort Time segments. A simple weighting system can be applied to alter the column average.

Further, it should also now be apparent to those skilled in the art that each RA, O, or RORA can be summarized over all time segments to determine an overall RA, O, or RORA (e.g. using averages or summations).

It should also now be apparent to those skilled in the art that the method and the system of the present invention transforms economic and eligibility information produced over calendar/clock time (CCT) per a unique unit of analysis (e.g. UOA-ID) that meets the criteria for inclusion into a specific Population (Type or Grouper) into information organized by Cohort Time and summarized across all UOA-IDs that are part of the same Population and that can be subdivided into mutually exclusive categories through the use of CATVAR. This is accomplished by determining the time segment and its duration, the population in which the UOA-ID is entered (based on Type), the value of some economic variable (VAR Value), and the potential and eligibility of the UOA-ID per time segment, with the provision that it be subdivided by CATVAR. As previously described, the Population is based on a criterion or a set of criteria (Type) that a UOA-ID must meet to be a member. The time/date at which the UOA-ID meets the Type is the "Start Time." The VAR Value is an economic variable that can be specified or calculated and can be fixed or variable per each time segment or fixed or variable per UOA-ID. The potential eligibility score is based on the time of the study and method of the present invention has application across a wide range of businesses and industries including, but not limited to, health care industries, insurance industries, manufacturing industries, the marketing and advertising industries, travel industries, and retail industries. For example, the method of the present invention can be easily translated for warranty applications, actuarial applications, insurance applications, marketing and advertising applications, frequent use program applications, shopping card applications, trademark/trade dress/product design evaluation applications, infringement applications, etc.

Accordingly, the present invention is a method and system to qualitatively analyze cost reduction programs and for analyzing data for optimizing the allocation of resources to best serves a business' goals. The method and apparatus transforms this information into usable estimates of resource allocation needed to achieve specified outcomes and needed to determine the most optimal use of the resource allocation.

Although the foregoing invention has been described in some detail for purposes of clarity of understandings, it will be apparent that certain changes and modifications may be practiced within the scope of the appended claims. Furthermore, it should be noted that there are alternative ways of implementing both the method and system for implementing the method of the present invention. Accordingly, the present embodiments are to be considered as illustrative and not restrictive, and the invention is not to be limited to the details given herein, but may be modified within the scope and equivalents of the appended claims.

I claim:

1. A system for performing a study of analyzing resource allocation comprising:
   system software; and
   a central processing unit for implementing said system software, wherein said system software operates to perform the method having the steps of:
   identifying at least one criterion for inclusion into a specific population;
   identifying sets of information wherein each set of information includes a particular Individual Unit of Analysis entity involved in the study (UOA-ID), a Calendar Clock date/time (CCT), a Categorical Variable (CATVAR), and a Variable Value (VAR Value);
   grouping each UOA-ID from said sets of information into the appropriate said specific population (Type);
   identifying a Start Time wherein each UOA-ID has met said at least one criterion;
   forming at least one prospective or retrospective Cohort time segment for each UOA-ID based on their Start Time;
   placing each UOA-ID into the appropriate said Cohort time segment;
   calculating an eligibility score for each UOA-ID for each said Cohort time segment;
   calculating an Eligible Adjusted Variable Value for each UOA-ID for each said Cohort time segment; and
   generating at least one Output Expression showing at least one trend of a particular population, said at least one trend expressed in at least one of said Cohort time segments and wherein said at least one Output Expression is based on said Eligible Adjusted Variable Value and said UOA-ID for each said Cohort time segment and wherein at least one Output Expression is subdivided by each said CATVAR;
   and wherein the system further includes analyzing and evaluating a resource allocation utilizing the generated said at least one Output Expression.

2. The system of claim 1 wherein said method further comprising the step of transforming said at least one Output Expression from being expressed in Cohort time segments to being expressed in CCT segments that are subdivided by each said CATVAR.

3. The system of claim 1 wherein said at least one trend relates to health care.

4. The system of claim 1 wherein said at least one trend relates to the group consisting of warranty applications, actuarial applications, insurance applications, marketing and advertising applications, frequent use program applications, shopping card applications, trademark/trade dress/product design evaluation applications, web page applications, infringement applications, and health care applications.

5. The system of claim 1 wherein each said Output Expression is generated by calculating an Eligible Adjusted Variable Value (EAV) based on a summary metric for each UOA-ID per Type subdivided by each CATVAR.

6. The system of claim 1 wherein said method further comprising the steps of:
   determining a Dichotomous Variable (DV) per Type per time segment;
   calculating an Eligible Adjusted Variable Value (EAV) summary metric for all UOA-IDs per Type per time segment; and
   calculating an EAV Net Value per Type per time segment subdivided by each CATVAR to generate at least one Output Expression.

7. The system of claim 1 wherein said method further comprising the steps of:
   determining a Return On Resource Allocation (RORA);
   determining an Outcome;
   calculating a Number Needed to Target (NNT);
   calculating an Eligible Adjusted Variable Value (EAV) Net Value per Type per time segment; and
   calculating the maximum available Resource Allocation (RA) per UOA-ID per time segment subdivided by each CATVAR to generate said at least one Output Expression.

8. The system of claim 1 wherein said method further comprising the steps of:
   determining a Resource Allocation (RA);
   determining an Outcome;
   calculating a Number Needed To Target (NNT);
   calculating an Eligible Adjusted Variable Value (EAV) Net Value per Type per time segment; and
   calculating the Return On Resource Allocation (RORA) per UOA-ID per time segment subdivided by each CATVAR to generate said at least one Output Expression.

9. The system of claim 1 wherein said method further comprising the steps of:
   determining a Return On Resource Allocation (RORA);
   determining a Resource Allocation (RA);
   calculating a Number Needed To Target (NNT);
   calculating an Eligible Adjusted Variable Value (EAV) Net Value per Type per time segment; and
   calculating an Output per UOA-ID per time segment subdivided by each CARVAR to generate said at least one Output Expression.

10. A system for improving resource allocation using a plurality of sets of information the system comprising:
    system software; and
    a central processing unit for implementing said system software, wherein said system software operates to perform the method comprising the steps of:
    for each set of information, identifying a particular Individual Unit of Analysis (UOA-ID), a specific population, at least one Categorical Variable (CATVAR values), a Calendar Clock date/time for each UOA-ID (CCT) and a Variable Value (VAR);
    grouping each UOA-ID into an appropriate Grouper;
    identifying a Start Time wherein said Start Time is the earliest CCT for each specific UOA-ID per said specific population (Type);
    identifying a time segment duration;
    forming time segments based on the Start Time wherein each UOA-ID meet certain eligibility criterion;
    adjusting and standardizing each VAR to create Eligible Adjusted Variable Values (AdjVAR Values);
    placing each AdjVAR Values into the appropriate time segment;
    calculating an eligibility score for each UOA-ID; and
    generating at least one Output Expression per each said CATVAR values which are compared to each other for analyzing and evaluating a resource allocation showing at least one trend of a particular population, said at least one trend expressed in at least one of said Cohort time segments and wherein said at least one Output Expression is based on said Eligible Adjusted Variable Value and said UOA-ID for each said Cohort time segment;

and wherein the system further includes analyzing and evaluating a resource allocation utilizing the generated said at least one Output Expression.

11. The system of claim 10 wherein said method further comprising the step of transforming said at least one Output Expression from being expressed in Cohort time segments to being expressed in CCT segments and wherein said at least one Output Expressions is divided by each said CATVAR value which are then compared to each other.

12. The system of claim 10 wherein said at least one trend relates to health care.

13. The system of claim 10 wherein said at least one trend relates to insurance, marketing and advertising, frequent use programs, shopping cards, the Internet, trademark/trade dress/product design evaluation, patent and trademark infringement, and health care.

14. The system of claim 10 wherein said method further comprising the step of calculating an Eligible Adjusted Variable Value (EAV) based on a summary metric for each UOA-ID per Type and Output Expression per CATVAR values which are compared to each other.

15. The stem of claim 10 wherein said at least one Output Expression is generated by the steps of:
 determining a Dichotomous Variable (DV) per Type per time segment;
 calculating an Eligible Adjusted Variable Value (EAV) summary metric for all UOA-IDs per Type per time segment; and
 calculating an EAV Net Value per Type per time segment to generate said at least one Output Expression per each said CATVAR values which are compared to each other.

16. The system of claim 10 wherein each said at least one Output Expression is generated by said method further comprising the steps of:
 determining a Return On Resource Allocation (RORA);
 determining an Outcome;
 calculating a Number Needed to Target (NNT);
 calculating an Eligible Adjusted Variable Value (EAV) Net Value per Type per time segment; and
 calculating the maximum available Resource Allocation (RA) per UOA-ID per time segment to generate said at least one Output Expression per CATVAR values which are compared to each other.

17. The system of claim 10 wherein said at least one Output Expression is generated by said method further comprising the steps of:
 determining a Resource Allocation (RA);
 determining an Outcome;
 calculating a Number Needed To Target (NNT);
 calculating an Eligible Adjusted Variable Value (EAV) Net Value per Type per time segment; and
 calculating a Return On Resource Allocation (RORA) per UOA-ID per time segment and generate said at least one Output Expressions per CATVAR values which are compared to each other.

18. The system of claim 10 wherein each said at least one Output Expression is generated by said method further comprising the steps of:
 determining a Return On Resource Allocation (RORA);
 determining a Resource Allocation (RA);
 calculating a Number Needed To Target (NNT);
 calculating an Eligible Adjusted Variable Value (EAV) Net Value per Type per time segment; and
 calculating an Output per UOA-ID per time segment to generate said at least one Output Expressions per CATVAR values which are compared to each other.

19. A system for Performing a study of analyzing resource allocation whereby Output Expressions are produced comprising a representation, said representation is selected from the group consisting of a showing Eligible Adjusted Variable Value (EAV) trends for a specific Population having eligibility criteria and formed from individual units each meeting at least one defined criteria, said trends are expressed in Cohort time segments based on a Start Time wherein each individual unit meets all of the eligibility criteria to be included into the Population; a showing Number Needed to Target (NNT) trends of said specific Population; said trends are expressed in Cohort time segments per Categorical Variable (CATVAR) values which are compared to each other.

* * * * *